United States Patent [19]

Kido et al.

[11] Patent Number: 4,869,114

[45] Date of Patent: Sep. 26, 1989

[54] LIQUID DEPOSITING DEVICE AND METHOD

[75] Inventors: Keishiro Kido; Sigeru Tezuka, both of Saitama, Japan

[73] Assignee: Fuji Photo Film Co., Ltd., Kanagawa, Japan

[21] Appl. No.: 277,817

[22] Filed: Nov. 30, 1988

[30] Foreign Application Priority Data

Dec. 4, 1987 [JP] Japan ................. 62-307064

[51] Int. Cl.[4] ............................................. G01N 1/14
[52] U.S. Cl. .................................................. 73/864.24
[58] Field of Search ........... 73/864.11, 864.13, 864.24, 73/864.25; 141/130; 422/68–70, 100; 222/420; 210/198.3, 658

[56] References Cited

U.S. PATENT DOCUMENTS

| | | | |
|---|---|---|---|
| 3,449,959 | 6/1969 | Grimshaw | 73/864.24 |
| 3,635,094 | 1/1972 | Oberli | 73/864.24 |
| 3,748,907 | 7/1973 | Sahmel | 73/864.24 |
| 3,853,008 | 12/1974 | Hoffa et al. | 73/864.25 |
| 3,858,450 | 1/1975 | Jones | 73/864.24 |
| 3,915,651 | 10/1975 | Nishi | 73/864.16 |
| 4,004,548 | 1/1977 | Smola et al. | 210/198.3 |
| 4,555,957 | 12/1985 | Frankel et al. | 73/864.25 |
| 4,570,495 | 2/1986 | Terada | 73/864.25 |
| 4,598,596 | 7/1986 | Wiseman et al. | 73/864.25 |
| 4,737,344 | 4/1988 | Koizumi et al. | 422/100 |
| 4,800,762 | 1/1989 | Sugaya | 73/864.24 |

FOREIGN PATENT DOCUMENTS

| | | |
|---|---|---|
| 57-28356 | 12/1982 | Japan . |
| 61-231463 | 10/1986 | Japan . |
| 1531760 | 11/1975 | United Kingdom . |

Primary Examiner—Robert R. Raevis
Attorney, Agent, or Firm—Sughrue, Mion, Zinn, Macpeak & Seas

[57] ABSTRACT

A sample liquid is sucked into a nozzle which is mounted at a front end of an arm. Then the arm is moved down to a position where the sample liquid is discharged from the nozzle so as to form a drop on the lower end of the nozzle. Thereafter the arm is further moved down at a speed not higher than 40 mm/sec to a position where the drop comes into contact with a chemical analysis element.

9 Claims, 3 Drawing Sheets

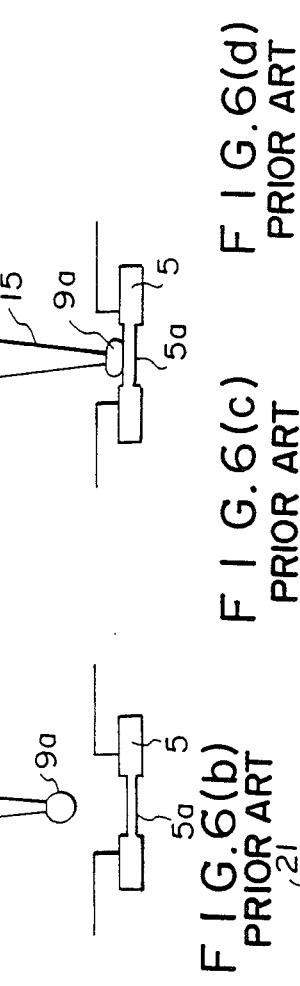
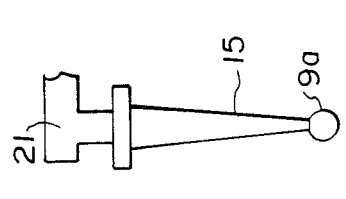
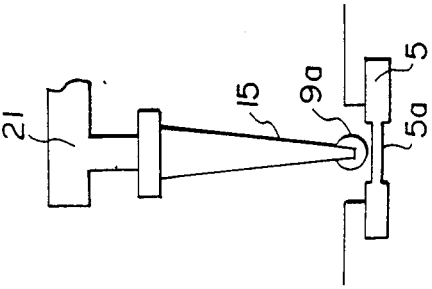
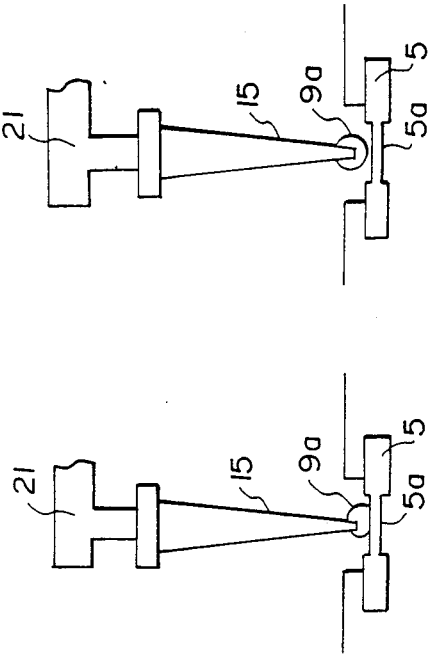
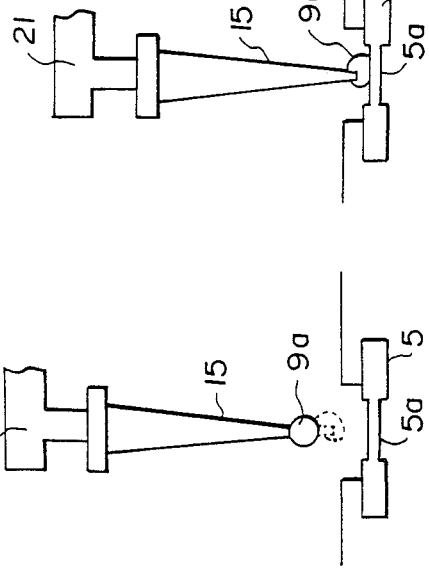
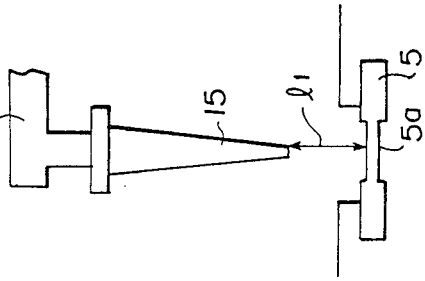

LIQUID DEPOSITING DEVICE AND METHOD

BACKGROUND OF THE INVENTION

1. Field of the Invention

This invention relates to a liquid depositing device for depositing a predetermined quantity of a sample liquid on a chemical analysis element such as a chemical assay slide and a method for carrying out the same. In particular, this invention relates to a liquid depositing device and a method for automatically depositing a sample liquid on a chemical analysis element.

2. Description of the Prior Art

When the concentration of a specific chemical substance in a body fluid, such as blood or urine, of an organism is to be determined by using a chemical analysis element such as a chemical assay slide, one must measure out a predetermined quantity of a sample liquid and deposit it on the analysis element with required accuracy. Liquid depositing devices to be used for this purpose are disclosed, for example, in Japanese Unexamined Utility Model No. 57(1982)-283656, Japanese Unexamined Patent Publication No. 60(1985)-155942, (corresponding to U.S. Pat. No. 4,737,344), British Pat. No. 1,531,760, and U.S. Pat. No. 3,915,651. With these liquid depositing devices, however, it is difficult to change the quantity of the liquid to be discharged from the device by remote control because the position of the stopper for limiting the motion of the piston thereby controlling the quantity of the discharged liquid must be changed.

In U.S. Ser. No. 062,874 (filed June 16, 1987), which is assigned to Fuji Photo Film Co., Ltd., a liquid depositing device has been proposed in which the amount of a liquid to be discharged therefrom can be remote controlled. In this liquid depositing device, a liquid depositing tip is removably mounted on a tip mounting portion formed at one end of a tip support arm mounted for up-and-down movement. A suction-and-discharge mechanism is operatively connected to the liquid depositing tip by way of the tip support arm to suck sample liquid into the depositing tip and to discharge it from the depositing tip onto a chemical assay slide or the like. The quantity of the sample liquid to be sucked into the tip and to be discharged therefrom is controlled by a quantity control mechanism which controls the operation of the suction-and-discharge mechanism. The tip support arm is adapted to move up and down between a sucking position at which the depositing tip is mounted or removed, as required, and the sample liquid is sucked into the tip and a depositing position at which the lower end of the tip is positioned immediately above the liquid receiving layer of a chemical assay slide set at a predetermined position, the sucking position being higher than the depositing position.

However, when the liquid depositing device according to U.S. Ser. No. 062,874 is used in the above-mentioned manner, in some cases the sample liquid is deposited at an improper position or the quantity of the liquid deposited is less than required.

In a conventional device as shown in FIG. 6(a), a liquid depositing tip 15 held by a tip support arm 21 is moved down to a discharging position which is located above a liquid receiving layer 5a of a chemical assay slide 5 by a predetermined distance l, (about 8 mm, for example) after a sample liquid is sucked into the tip 15. At the discharging position, the sample liquid is discharged from the tip 15 in such a way that a drop of the liquid 9a is formed at the lower end of the tip 15. Then the tip 15 is moved down to a depositing position which is closer than the discharging position to the liquid receiving layer 5a. However, the drop of the liquid often rides up the surface of the tip 15 as indicated by the dotted line in FIG. 6(b). In some cases, after a few drops of the liquid have been deposited, the subsequent drop of the liquid discharged from the tip 15 does not land on the chemical assay slide 5.

SUMMARY OF THE INVENTION

In view of the foregoing, the object of the present invention is to improve the accuracy of a liquid depositing device, which deposits a quantity of a liquid on a chemical assay slide on the like.

In accordance with the present invention, an arm is stopped at a discharging position, where a sample liquid is discharged from a liquid depositing nozzle in such a way that a drop of the sample liquid is formed at the lower end of the liquid depositing nozzle, and then the liquid depositing nozzle is moved down from the discharging position at a controlled speed, in order to bring the drop of the liquid into contact with a chemical assay slide or the like.

The liquid depositing device and method in accordance with the present invention are characterized in that the end of the arm is moved down from the discharging position to the depositing position at the speed not higher than 40 mm/sec. In order to further improve the accuracy of the liquid depositing device in depositing a predetermined quantity of a sample liquid, it is preferable that the abovementioned speed does not exceed 20 mm/sec.

The device in accordance with the present invention is not likely to deform the drop of the sample liquid formed at the lower end of the liquid depositing nozzle nor the drop is likely to lean toward one side of the depositing nozzle. Accordingly, a predetermined quantity of sample liquid can be deposited repeatedly on a chemical assay slide or the like with sufficient accuracy.

BRIEF DESCRIPTION OF THE DRAWINGS

FIGS. 6(a), 6(b), 6(c) and 6(d) are schematic views showing the states of a drop of liquid at the end of the nozzle 15 as it is moved from the discharging position to the depositing position in a prior art device.

DESCRIPTION OF THE PREFERRED EMBODIMENT

The discharging position should be sufficiently above the depositing position so as to ensure that the liquid drop should not come into contact with the surface of the liquid-receiving layer of the chemical assay slide. The distance between the discharging position and the depositing position need not be much greater than the minimum required distance. It should be rather small as far as the requirement above is fulfilled, in view of the operational efficiency of the device. Specifically, the distance is preferably a few or several millimeters.

At the depositing positions, the lower end of the nozzle is placed so close to the surface of the liquid-receiving layer of the chemical assay slide that the liquid drop attached thereto comes into contact with the surface. It is preferred that the end of the nozzle itself does not come into contact with the surface of the slide, in order to avoid the possible damage of the surface due to the contact.

Figure 5:
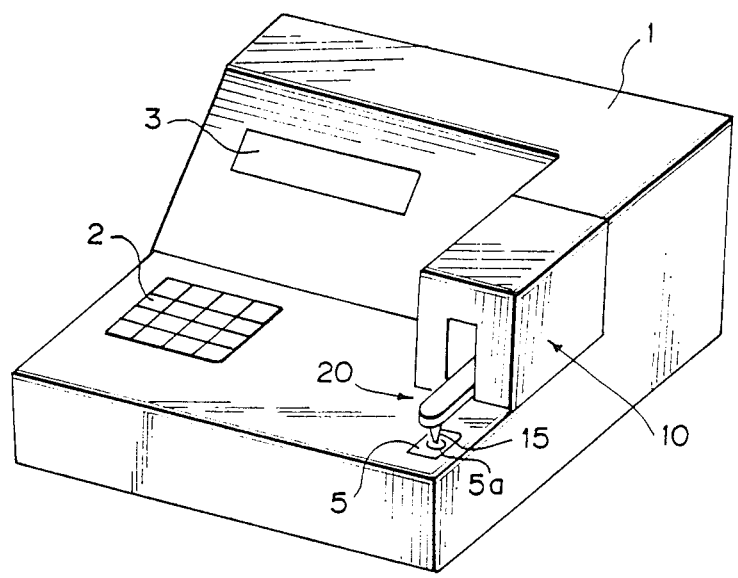
FIG. 5 is a perspective view showing a chemical assay system in which the liquid depositing device is employed.

FIG. 5 shows a chemical assay system provided with a liquid depositing device 10 in accordance with an embodiment of the present invention. The chemical assay system has a body 1 on which an input key board 2 and a display portion 3 are provided. The liquid depositing device 10 is mounted on the body 1. The display portion 3 is furnished for displaying data obtained from measurements made with the chemical assay system, and the like, and the operation of the display portion 3 and the liquid depositing device 10 are controlled from the input key board 2. The liquid depositing device 10 has an arm 20 projecting forward from one of its sides, which allows the arm 20 to move up-and-down. A depositing tip 15 is removably mounted on a projecting end portion of the arm 20, and a chemical assay slide 5 having a liquid receiving layer 5a is positioned on the body 1 below the depositing tip 15. The function of the liquid depositing device 10 is to automatically deposit a predetermined quantity of sample liquid on the liquid receiving layer 5a of the slide 5.

The liquid depositing device 10 will now be described in detail with reference to FIGS. 1 and 2. The liquid depositing device 10 comprises the arm 20, a suction-and-discharge mechanism 30 and an arm swinging mechanism 50 disposed in a box casing 11, and a controller 40 disposed in the body 1 and connected with the liquid depositing device 10 by way of a connector 41. The box casing 11 is a rectangular box and is placed on the body 1 by way of an adjustable length leg 12a and a pair of fixed legs 12b and 12c. The box casing 11 is provided on the front face with a vertical slot 11a which permits the arm 20 to project forward from the box casing 11 and to be swung up and down as shown by the chained line in FIG. 1.

The arm 20 comprises a base arm portion 22 pivotally mounted on the bottom of the box casing 11 by way of a pin 22a, and a front arm portion 21 fixed to the front end of the base arm portion 22 so as to project forward through the vertical slot 11a. At the front end of the front arm portion 21, a tip mounting portion 21b is formed such that it extends downward. The depositing tip 15 is provided with an inner space 15b and a suction-and-discharge port 15a communicating with the inner space 15b, and is removably mounted on the tip mounting portion 21b. A sample liquid passage 21a is formed in the front arm portion 21 and communicates with the inner space 15b of the depositing tip 15. The arm 20 is adapted to be swung (as indicated by arrow A) about the pin 22a with the depositing tip 15 mounted on the tip mounting portion 21b.

The suction-and-discharge mechanism 31 comprises a piston 31 fit into the rear end portion of the sample liquid passage 21a so that it may slide in it back and forth, a first driven gear 32 which engages the male threads of a worm 31a formed on the rear end portion of the piston 31 and supported on the base arm portion 22 in such a way that it may rotate, a first pinion 33 that meshes with the first driven gear 32, and a first pulse motor 34 for driving the first pinion 33. When the first pulse motor 34 is energized, the first driven gear 32 is rotated by way of the first pinion 33 and the piston 31 is slid back and forth (rightward and leftward in FIG. 1) by way of the engagement of the male threads of the worm 31a on the piston 31 with the first driven gear 32, whereby sample liquid can be sucked into the inner space 15b of the depositing tip 15, discharged through the suction-and-discharge port 15a and then deposited on the liquid receiving layer 5a of the slide 5.

The arm swinging mechanism 50 comprises a sector gear 51 firmly attached to the base arm portion 22 in such a way that it can rotate about the axis of pin 22a, a second pinion 52 which meshes with the sector gear 51, and a second pulse motor 53 for driving the second pinion 52. When the second pinion 52 is rotated by the second pulse motor 53, the sector gear 51 rotates about the pin 22a. Since the sector gear 51 is attached to the base arm portion 22, the base arm portion 22 rotates along with the sector gear 51 about the pin 22a, whereby the arm 20 is swung in the direction indicated by arrow A.

The controller 40 controls the first pulse motor 34 which in turn controls the quantity of sample liquid which is sucked into and discharged from the tip 15. Further, the controller 40 controls the second pulse motor 53, which moves arm 20.

Figure 3:
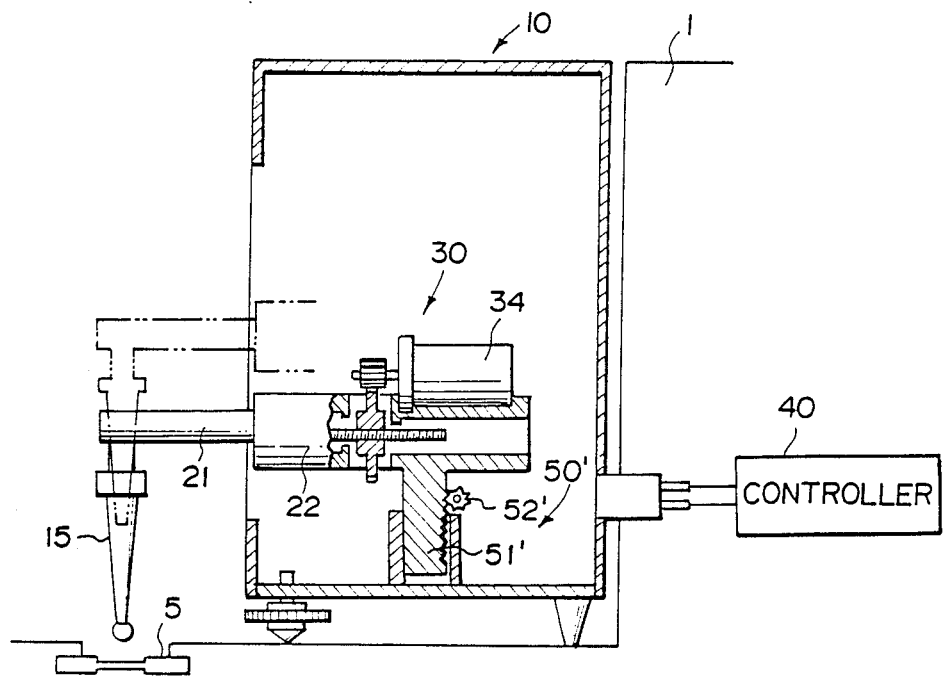
FIG. 3 is a cross-sectional view of a modification of the liquid depositing device shown in FIGS. 1 and 2, FIGS. 4(a) and 4(b) are schematic views respectively showing the states of a drop of sample liquid at the discharging position and the depositing position in a liquid depositing device in accordance with the present invention.

As shown in FIG. 3, instead of rotating about pin 22a, the arm 20 may be linearly slid up and down by means of an arm lift mechanism 50', comprising a vertical rack 51' attached to the base arm portion 22, a pinion 52' which meshes with the rack 51' and a pulse motor (not shown) for driving the pinion 52'.

Figure 1:
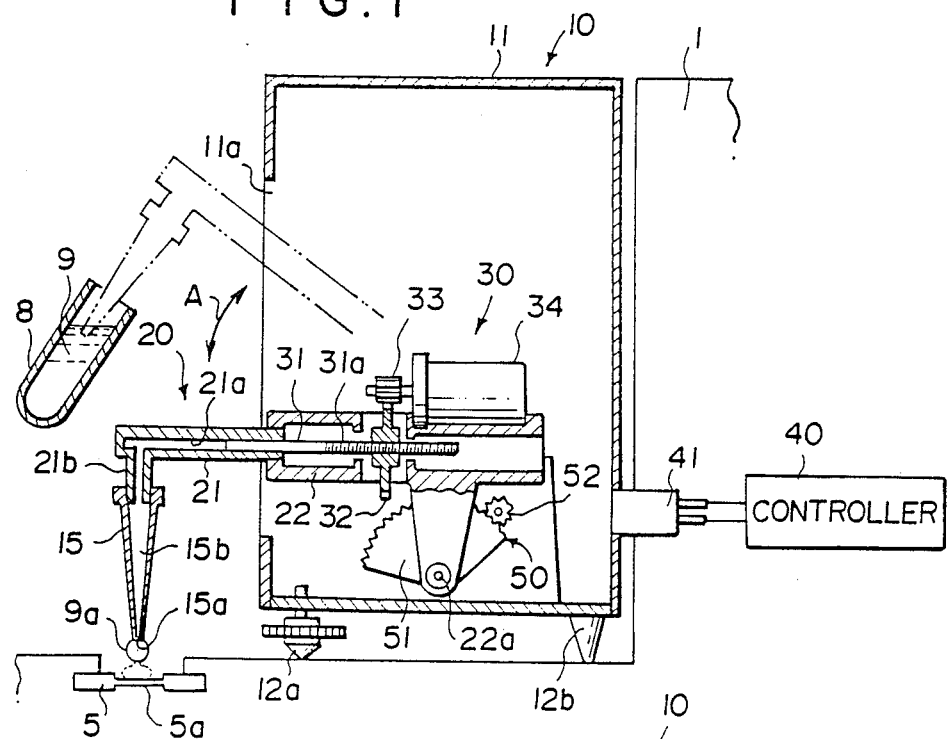
FIG. 1 is a cross-sectional view of a liquid depositing device in accordance with an embodiment of the present invention.
Figure 2:
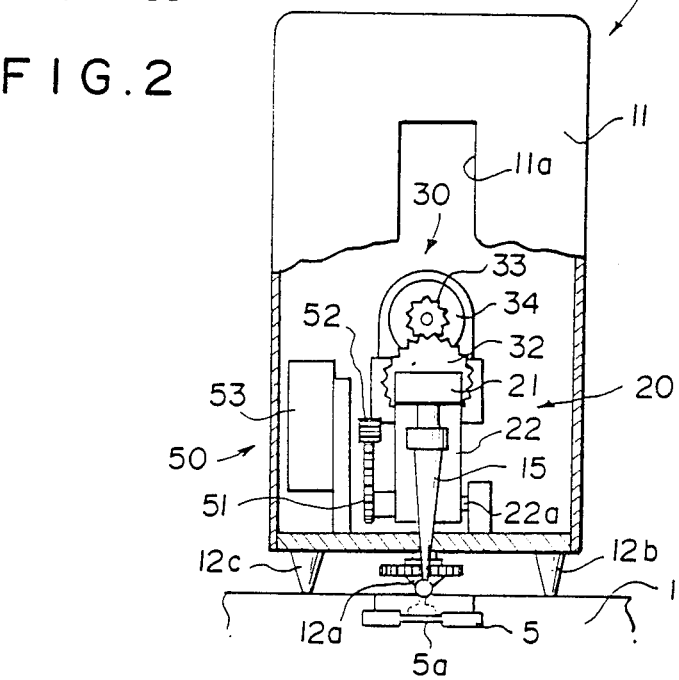
FIG. 2 is a front view of the liquid depositing device with its outer frame partly broken away.

When operating the liquid depositing device 10 of the embodiment shown in FIGS. 1 and 2, the second pulse motor 53 is first driven to swing the arm 20 upward (clockwise) about the pin 22a to a sucking position shown by the chained line in FIG. 1. In the sucking position, a new tip 15 is mounted on the tip mounting portion 22b. Then a sample container 8 with sample liquid 9 therein is manually brought and placed so that the lower end portion of the depositing tip is dipped into the sample liquid 9. Then the first pulse motor 34 is driven to move the piston 31 by a predetermined distance to the rear (to the right in FIG. 1), thereby sucking a predetermined quantity of the sample liquid 9 into the inner space 15b of the depositing tip 15. Then the second pulse motor 53 is driven to return the arm 20 to the discharging position, the lower position shown in FIG. 1. The arm 20 is temporarily stopped at this position.

In the discharging position, the port 15a of the depositing tip 15 is positioned a predetermined distance above the liquid receiving layer 5a of the chemical assay slide 5 placed below the depositing tip 15 on body 1. At the discharging position, the first pulse motor 34 is driven so as to move the piston 31 forward (to the left in FIG. 1) by a distance which causes a drop 9a of the sample liquid 9 held in the inner space 15b of the tip 15 to be discharged from the port 15a. This drop 9a of the predetermined quantity of the sample liquid 9 is formed at the lower end of the tip 15 as shown in FIGS. 1 and 2. After the drop 9a is formed, the depositing tip 15 is moved further down so that the drop 9a comes into contact with the liquid receiving layer 5a, as shown by the dotted line in FIGS. 1 and 2.

In this embodiment, the discharging tip 15 is moved down from the discharging position, where the drop 9a is formed, to the depositing position, where the drop 9a comes into contact with the liquid receiving layer 5a, by driving the second pulse motor 53. Pulse motor 53 rotates its shaft a specific number of degrees for each pulse it receives. Therefore, the distance between the discharging position and the depositing position is determined by the number of pulses sent by the controller 40 to motor 53, and the speed at which the depositing tip 15 is moved down depends on the interval of time between consecutive pulses sent to the motor 53. In accordance with the present invention, the speed at which the depositing tip is moved down is less than 40 mm/sec. When the depositing tip 15 is moved down at a speed higher than 40 mm/sec, the drop 9a may not be deposited on the liquid receiving layer, accurately, i.e. at a desired spot on the liquid receiving layer 5a. In order to further improve the accuracy of the liquid depositing device 10 in depositing a predetermined quantity of a sample liquid, the speed at which the depositing tip 15 is moved down is preferably not higher than 20 mm/sec. However, the speed is preferably not lower than about 5 mm/sec to ensure that the device works efficiently.

By using VTR, the states of several drops 9a were observed as the depositing tip 15 was moved down and as drops 9a were deposited on the liquid receiving layer 5a. During these observations the speed at which the tip 15 was moved down was changed. These observations confirmed that, when the depositing tip 15 is moved down from the discharging position to the depositing position at a speed not higher than 40 mm/sec., the drop 9a formed at the discharging position shown in FIG. 4(a) does not lean away from the center of the tip 15, nor does it ride up the surface of the tip 15 (as shown in FIG. 6(b)) as the tip 15 is moved down. Accordingly, a predetermined quantity of sample liquid is deposited at a proper position as shown in FIG. 4(b). The drop 9a does not lean off center as shown in FIG. 6(c) nor does it fail to contact the liquid receiving layer 5a as shown in FIG. 6(d).

By controlling the first and second pulse motors 34 and 53 in the manner described above, the sample liquid 9 is sucked into the depositing tip 15 and deposited on the liquid receiving layer 5a accurately. The pulse motors 34 and 53 are controlled by signals sent to them from the controller 40 over connector 41. The controller 40 can be operated from the key board 2 or the like.

By controlling the first pulse motor 34 with the controller 40, the quantity of the sample liquid sucked into the depositing tip 15 and the quantity of the same discharged from the depositing tip 15 can be easily controlled. Since the speed at which the depositing tip is moved down is adjusted to fall within the above-specified range, the drop of sample liquid is properly deposited on the liquid receiving layer 5a of the chemical assay slide 5.

Since the quantity of the sample liquid to be sucked into and discharged from the depositing tip 15 generally depends on the type of slide 5 used and the like, it is preferred that the quantity of the sample liquid be automatically determined by having a means in the chemical assay system for reading a bar code or the like provided on the chemical assay slide 5. The bar code indicates the quantity of the sample liquid to be deposited on the specific slide. Information about the quantity of the sample liquid may also be manually input into the controller 40 from the key board 2.

The invention has been described in detail with reference to certain preferred embodiments thereof, but it will be understood that variations and modification can be effected within the spirit and scope of the invention.

For example, the depositing tip 15 may be fixed to the front end of the arm 20. Also, the suction-and-discharge mechanism 30 may be connected to the depositing tip 15 by way of a flexible tube, or the like, bypassing the arm 20. Further, a continuously-supplied chemical assay tape, a stick-like assay member, or the like, can be used in place of the chemical assay slide 5.

We claim:

1. A liquid depositing device comprising:
   an arm adapted to move up and down;
   a liquid depositing nozzle mounted at a front end of said arm;
   a suction-and-discharge means operatively connected to said liquid depositing nozzle, and
   a quantity control means which controls the operation of said suction-and-discharge means which in turn controls the quantity of the sample liquid sucked into said liquid depositing nozzle and discharged therefrom;
   a lower end of said liquid depositing nozzle being moved, in accordance with movements of said arm, between a sucking position where said sample liquid is sucked into said liquid depositing nozzle and a depositing position, which is located lower than said sucking position, said arm being adapted to stop temporarily at a discharging position which is located between said sucking position and said depositing position but closer to said depositing position, said sample liquid being discharged from said liquid depositing nozzle at said discharging position so that a drop of said sample liquid is formed at the lower end of said liquid depositing nozzle, and said arm being adapted such that said liquid depositing nozzle moves down at a speed of not higher than 40 mm/sec from said discharging position to said depositing position after the drop of said sample liquid is formed at the lower end of said liquid depositing nozzle.

2. A liquid depositing device as defined is claim 1 in which said arm is adapted to rotate around a horizontal axis.

3. A liquid depositing device as defined in claim 1 in which said liquid depositing nozzle comprises a tip mounting portion which is mounted at the front end of said arm, and a liquid depositing tip which is detachably attached to said tip mounting portion.

4. A liquid depositing device as defined in claim 1 in which said suction-and-discharge means is located in said arm and operatively connected to said liquid depositing nozzle.

5. A liquid depositing device as defined in claim 1 in which said liquid depositing nozzle is moved down from said discharging position to said depositing position at a speed of not higher than 20 mm/sec.

6. A method for depositing a sample liquid on a dry-type chemical analyzer device by using a liquid depositing device;
   said liquid depositing device comprising:
   an arm adapted to move up and down;
   a liquid depositing nozzle mounted at a front end of said arm;

a suction-and-discharge means operatively connected to said liquid depositing nozzle; and a quantity control means which controls the operation of said suction-and-discharge means which in turn controls the quantity of the sample liquid to be sucked into said liquid depositing nozzle and to be discharged therefrom;

a lower end of said liquid depositing nozzle being moved, in accordance with movements of said arm, between a sucking position where said sample liquid is sucked into said liquid depositing nozzle and a depositing position which is located lower than said sucking position;

said method comprising the steps of:

sucking said sample liquid into said liquid depositing nozzle when said liquid depositing nozzle is positioned at said sucking position;

moving the lower end of said liquid depositing nozzle down to a discharging position which is located between said sucking position and said depositing position but closer to said depositing position;

stopping said liquid depositing nozzle at said discharging position;

discharging said sample liquid from said liquid depositing nozzle at said discharging position so as to form a drop of said sample liquid at the lower end of said liquid depositing nozzle;

moving the lower end of said liquid depositing nozzle down from said discharging position to said depositing position at a speed of not higher than 40 mm/sec;

and then bringing said drop into contact with said dry-type chemical analyzer device.

7. A method as defined in claim 6 wherein said arm rotates around a horizontal axis.

8. A method as defined in claim 6 wherein said sample liquid is blood plasma or blood serum.

9. A method as defined in claim 6 wherein said arm moves vertically.

* * * * *